United States Patent
Matsumura

(10) Patent No.: US 8,098,921 B2
(45) Date of Patent: Jan. 17, 2012

(54) ELASTIC IMAGE DISPLAY METHOD AND ELASTIC IMAGE DISPLAY DEVICE

(75) Inventor: Takeshi Matsumura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 817 days.

(21) Appl. No.: 12/161,434

(22) PCT Filed: Jan. 19, 2007

(86) PCT No.: PCT/JP2007/050796
§ 371 (c)(1),
(2), (4) Date: Jul. 18, 2008

(87) PCT Pub. No.: WO2007/083745
PCT Pub. Date: Jul. 26, 2007

(65) Prior Publication Data
US 2010/0220901 A1  Sep. 2, 2010

(30) Foreign Application Priority Data
Jan. 20, 2006  (JP) ................................ 2006-012513

(51) Int. Cl.
G06K 9/00 (2006.01)
A61B 8/00 (2006.01)
(52) U.S. Cl. ....................................... 382/133; 600/438
(58) Field of Classification Search .................. 382/128, 382/133; 600/437, 438
See application file for complete search history.

(56) References Cited

U.S. PATENT DOCUMENTS

| 5,441,052 A | 8/1995 | Miyajima |
| 5,474,070 A * | 12/1995 | Ophir et al. .................. 600/437 |
| 2004/0260180 A1 | 12/2004 | Kanai et al. |
| 2005/0085728 A1 | 4/2005 | Fukuda |

FOREIGN PATENT DOCUMENTS

| EP | 1 421 905 A1 | 5/2004 |
| JP | 62-72334 | 4/1987 |
| JP | 5-317313 | 12/1993 |
| JP | 6-245933 | 9/1994 |
| JP | 7-265303 | 10/1995 |
| JP | 2000-60853 | 2/2000 |
| JP | 2003-575 | 1/2003 |
| JP | 2004-267464 | 9/2004 |
| JP | 2005-144155 | 6/2005 |
| WO | WO 03/015635 A1 | 2/2003 |

* cited by examiner

Primary Examiner — Rochelle-Ann J Blackman
(74) Attorney, Agent, or Firm — Antonelli, Terry, Stout & Kraus, LLP.

(57) ABSTRACT

According to a 2-dimensional map having longitudinal and horizontal axes indicating different elastic information, hue or luminance of each pixel is mapped correspondingly to their elastic information, and the elastic information is combined to construct one elastic image. With this, a plurality of items of elastic information can be combined into one elastic image and displayed, and thereby the elastic image can be scanned in real time while observing it. Even where one item of elastic information may be in a gray zone, i.e., benign or malignant, another item of information may definitely show the differentiation between benign or malignant, and therefore highly accurate differentiation is possible. In addition, the user can perform diagnosis with the elastic image into which the plurality of items of elastic information is combined without moving the line of sight, thereby obtaining an improved visibility.

24 Claims, 12 Drawing Sheets

FIG.4
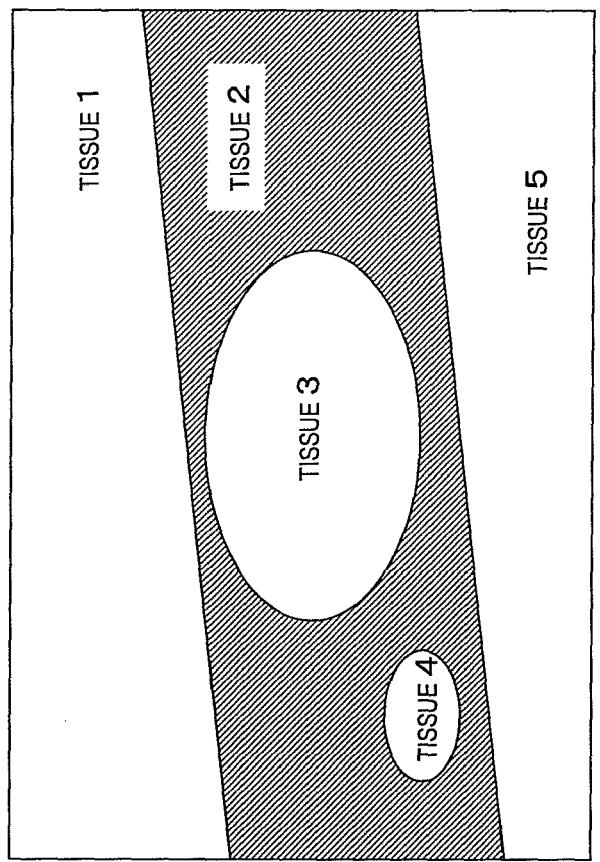
(A)
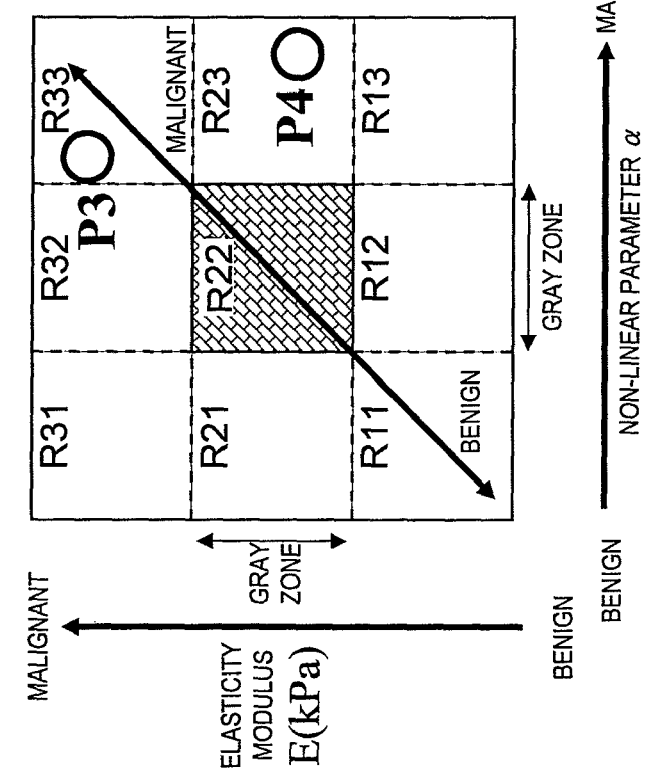
(B)

FIG.7

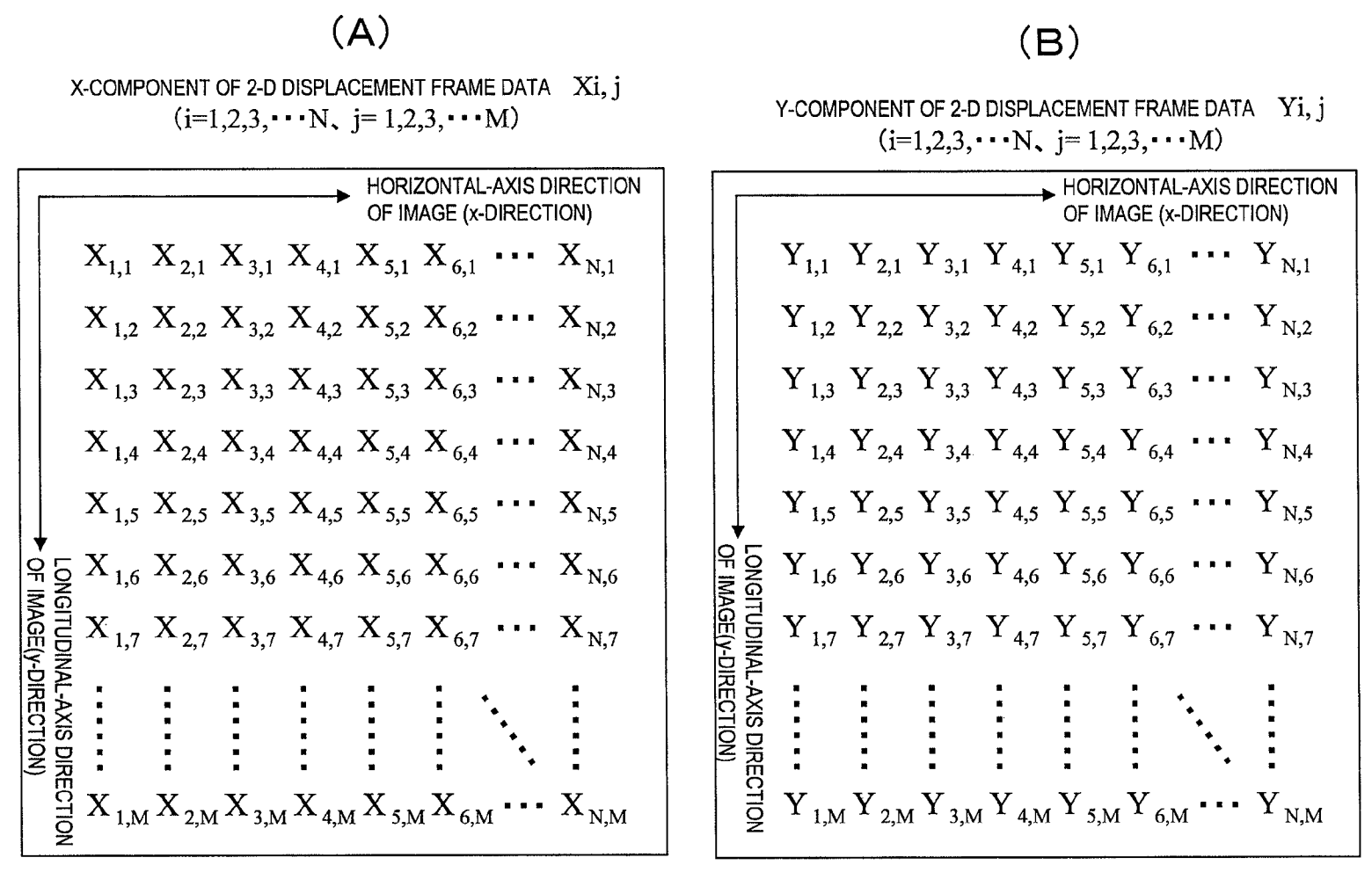

(A) X-COMPONENT OF 2-D DISPLACEMENT FRAME DATA $X_{i,j}$
$(i=1,2,3,\ldots N,\ j=1,2,3,\ldots M)$ (B) Y-COMPONENT OF 2-D DISPLACEMENT FRAME DATA $Y_{i,j}$
$(i=1,2,3,\ldots N,\ j=1,2,3,\ldots M)$ FIG.8
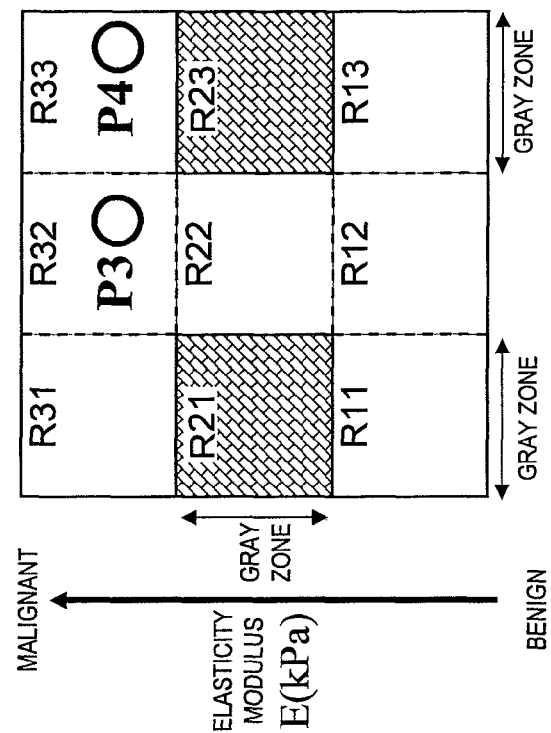
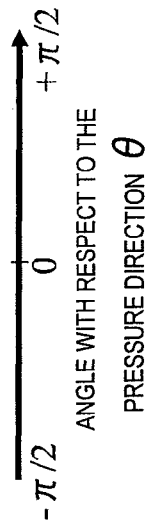

FIG.9
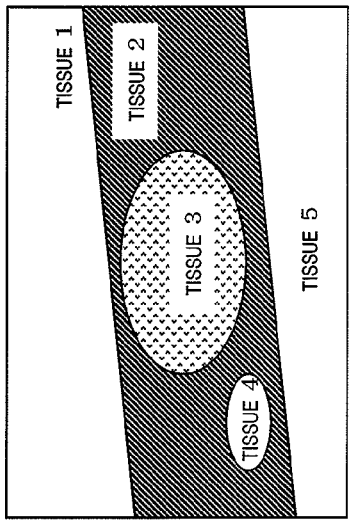
(C) MALIGNANT PROBABILITY IMAGE BY NON-LINEAR PARAMETER α
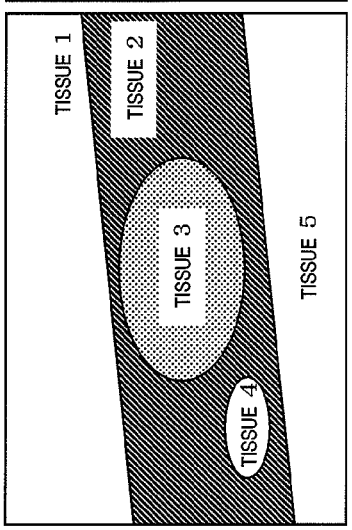
(B) MALIGNANT PROBABILITY IMAGE BY VISCOELASTICITY MUDULUS
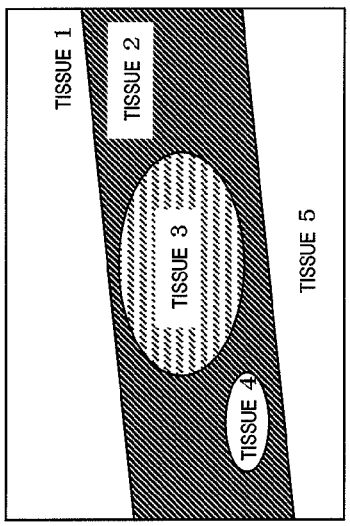
(D) MALIGNANT PROBABILITY IMAGE TO USE FOR THE FINAL DIAGNOSIS
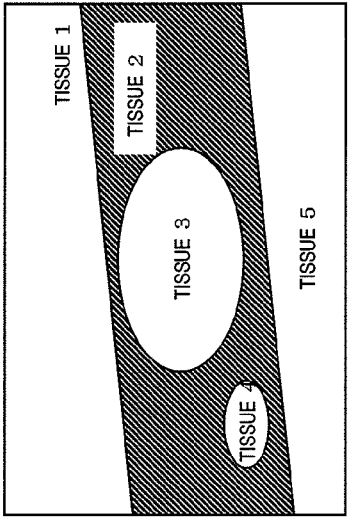
(A) MALIGNANT PROBABILITY IMAGE BY ELASTICITY MUDULUS

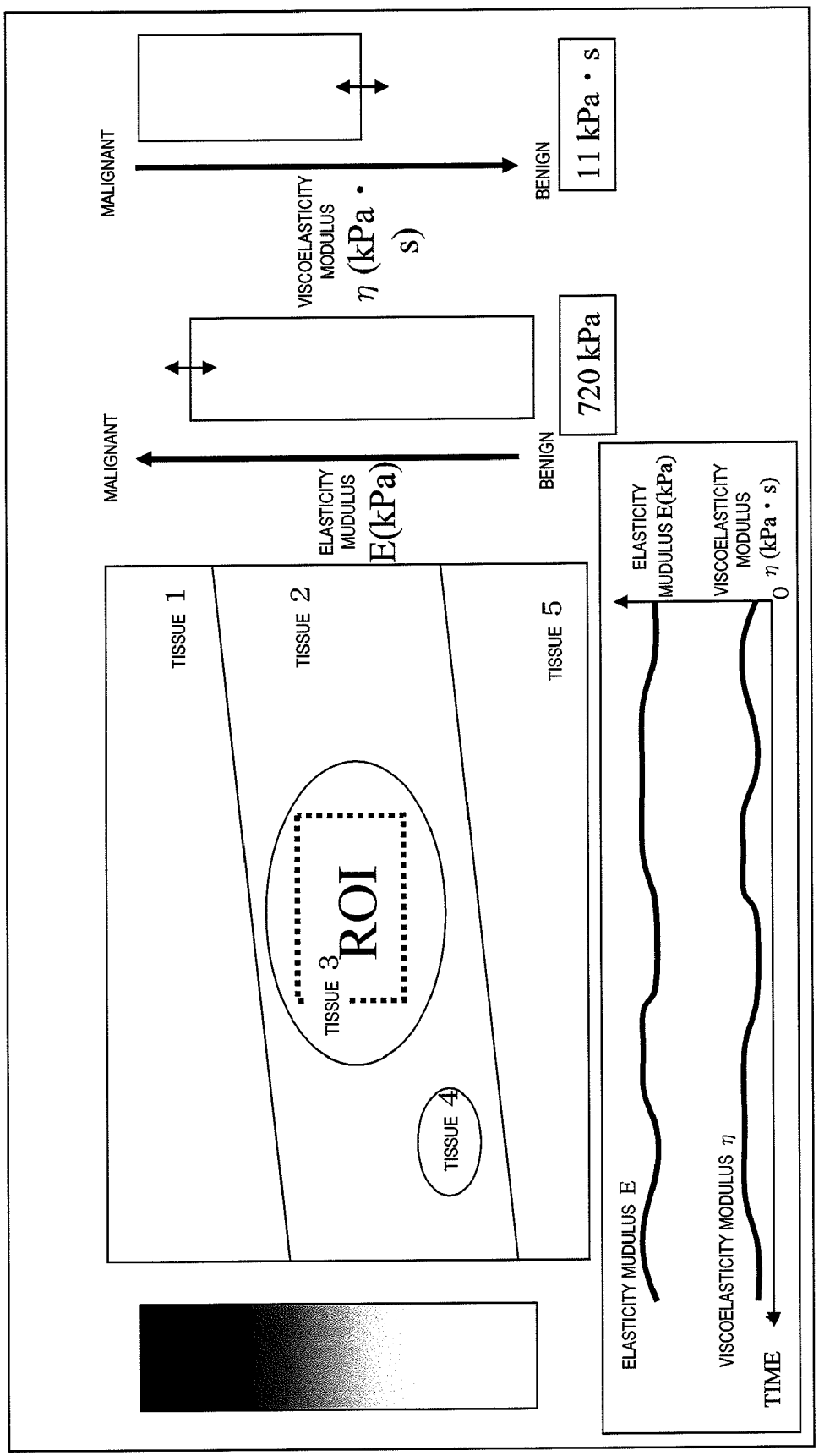

ELASTIC IMAGE DISPLAY METHOD AND ELASTIC IMAGE DISPLAY DEVICE

TECHNICAL FIELD

The present invention relates to an elastic image display method and elastic image display device, more particularly to the elastic image display method and elastic image display device effective in observing an elastic image indicating elastic information of biological tissues and perform diagnosis of benignancy or malignancy of the diseased area.

BACKGROUND ART

The diseased area such as a tumor of biological tissues is diagnosed, since the tissues are harder than the other normal tissues, by constructing an elastic image of the cross-section of a living body including the target region based on the elastic information wherein the elasticity of the biological tissues are measured by an ultrasonic diagnostic apparatus or magnetic resonance imaging apparatus. The relevant prior art is disclosed in Patent Documents 1 and 2.

As for an elastic image, for example, for an ultrasonic diagnostic apparatus, an image such as a displacement distribution image constructed by obtaining displacement of the biological tissues while the pressure is added to the target region, strain image obtained based on the previously acquired displacement, and an elasticity modulus image obtained based on the strain and stress of the respective regions of the biological tissues are generally known. These elastic images are suitable for screening tests since they can be acquired in real time. Such elastic images are generally colored by color mapping in accordance with the elastic information.

Patent Document 1: JP-A-H5-317313
Patent Document 2: JP-A-2000-60853

DISCLOSURE OF THE INVENTION

Problems to be Solved

However, for example, elasticity of cancer cells, depending on the region or individual variability, is often approximated to the elasticity of normal biological tissues (for example, fiber tissues), and is often difficult to accurately distinguish benignancy and malignancy even by observing the elastic image which is color mapped in accordance with the elasticity.

For example, in the case of breast disease, benign tumor is usually soft and the elasticity modulus thereof is 10~300 [kPa], and malignant tumor is often hard and the elasticity modulus thereof is 250~750 [kPa]. Thus, the range of 250~300[kPa] where the elasticity modulus of benign tumor and malignant tumor overlap turns out to be the gray zone that can be determined as either benign or malignant. In such case, diagnosis of benignancy or malignancy in tissues of the target region can be performed through measuring elastic information other than elasticity modulus and comprehensively evaluating the findings thereof. Items of elastic information other than elasticity modulus are, for example, an elastic image exhibiting viscoelasticity modulus considering the time wherein the biological tissues being pressed return to the original condition, or an elastic image having nonlinearity of elasticity modulus with respect to the strain as an index.

However, when conclusive evidence can not be obtained by one elastic image, since the same target region needs to be observed for evaluation by switching to the other elastic images, the operation becomes complicated and time consuming whereby lowering the test efficiency, and requires extra burdens to a patient.

Also, even when a plurality of elastic images are simultaneously obtained and displayed on the same screen, in the scanning operation for searching the target region in real time, it is impossible to observe the plurality of elastic images at once. Therefore, when the scanning operation is performed while observing one elastic image and the target region of the elastic image belongs to the elastic information of the gray zone, it is necessary to shift the line of sight to the other elastic image, which can eventually lead to a false recognition. Moreover, since the plurality of elastic images need to be displayed on a limited screen, size of the respective elastic images also need to be small which causes a problem of poor visibility.

The objective of the present invention is to provide an elastic image display method and elastic image display device with improved accuracy of differentiating benignancy and malignancy of tissues in the gray zone of elastic images, with superior visibility and real-time effectivity.

Means to Solve the Problems

In order to achieve the above-described objective, the first embodiment of the elastic image display method and elastic image display device of the present invention is characterized in synthesizing a plurality of items of elastic information and displaying them as one elastic image. By such method, since the plurality of items of elastic information are synthesized into one elastic image and displayed, it is possible to perform scanning operation in real time while observing the elastic image. Furthermore, in the case that one item of elastic information belongs to the gray zone of benignancy or malignancy and the other item of elastic information clearly defines benignancy or malignancy, the tissues can be differentiated with high-accuracy. Particularly, in accordance with the elastic image into which the plurality of items of information is combined, diagnosis can be performed without moving the line of sight, whereby leading to the improvement of visibility.

Also, in accordance with the present invention, since differentiation of the tissues can be performed with high-accuracy in one scanning operation in real time, test efficiency can be drastically improved. It also reduces the burden of a patient considerably since the possibility for reexamination can be reduced. This method can also be applied to detailed examination to improve the examination efficiency.

In the first embodiment of the present invention, the one elastic image can be constructed, in compliance with the two-dimensional map having two items of the elastic information as a longitudinal axis and a horizontal axis, by allocating hue or luminance to the respective pixels in accordance with the two items of elastic information. Also, in place of the above-described method, the one elastic image can be constructed by converting the different plurality of items of elastic information into an evaluated value for evaluating malignancy, and allocating hue or luminance of the respective pixels in accordance with the evaluated value of the respective items of elastic information.

Also, a second embodiment of the elastic image display method and elastic image display device of the present invention is capable of constructing an elastic image by comparing a plurality of items of information that are different from each other being set in the same target region using at least one of numeric values, line maps and graphic forms.

In this case, the one elastic image can be constructed by converting the plurality of items of elastic information in the target region that are different from one another into an evaluated malignancy value, and comparing the evaluated values of the plurality of items of elastic information using bar charts to be displayed. Also, in place of such method, the one elastic image can be constructed by comparing time variation of the plurality of items of information in the target region that are different from each other using line maps to be displayed.

Here, the different plurality of items of elastic information to be applied is the items such as:

nonlinear parameter related to the nonlinearity of elasticity modulus with respect to the elasticity modulus, viscoelasticity modulus and strain amount;

S/N judging information related to reliability of local dispersion included in the calculation result of the displacement or calculation result of coefficient correlation, etc.; and compressing direction, displacement, stress, strain, Poisson's ratio, strain ratio between two target regions to be added to the respective measuring points.

Effect of the Invention

In accordance with the present invention, it is possible to improve accuracy in differentiating benignancy and malignancy of biological tissues in the gray zone of an elastic image, and to provide an elastic image display method and elastic image display device with superior visibility without losing real-time efficiency.

BRIEF DESCRIPTION OF THE DIAGRAMS

FIG. 4 shows a two-dimensional color map and a color elastic image in practical example 1 of the embodiment 1.

Figure 5:
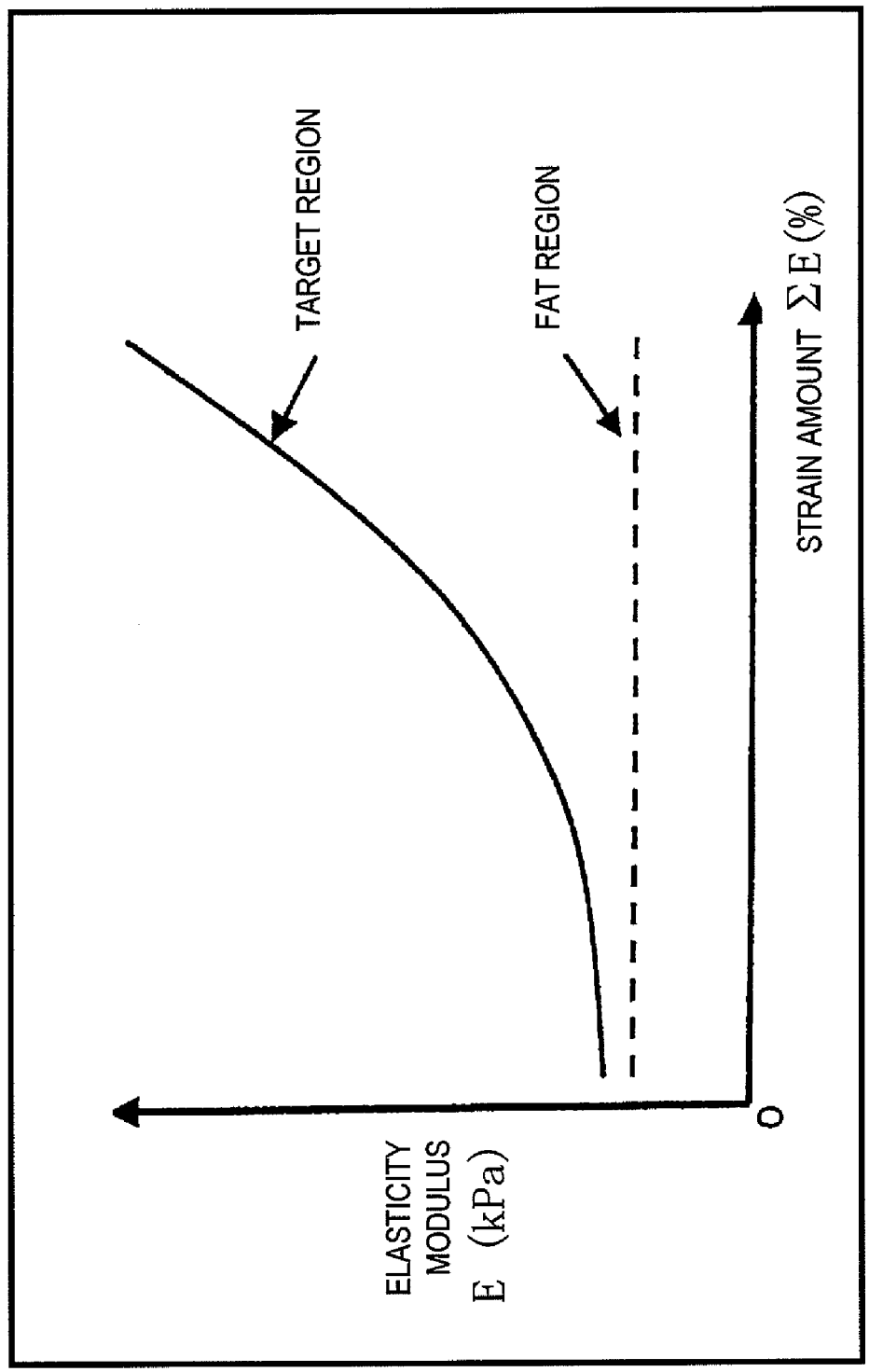

FIG. 5 explains nonlinearity of elasticity modulus with respect to the strain amount.

Figure 6:
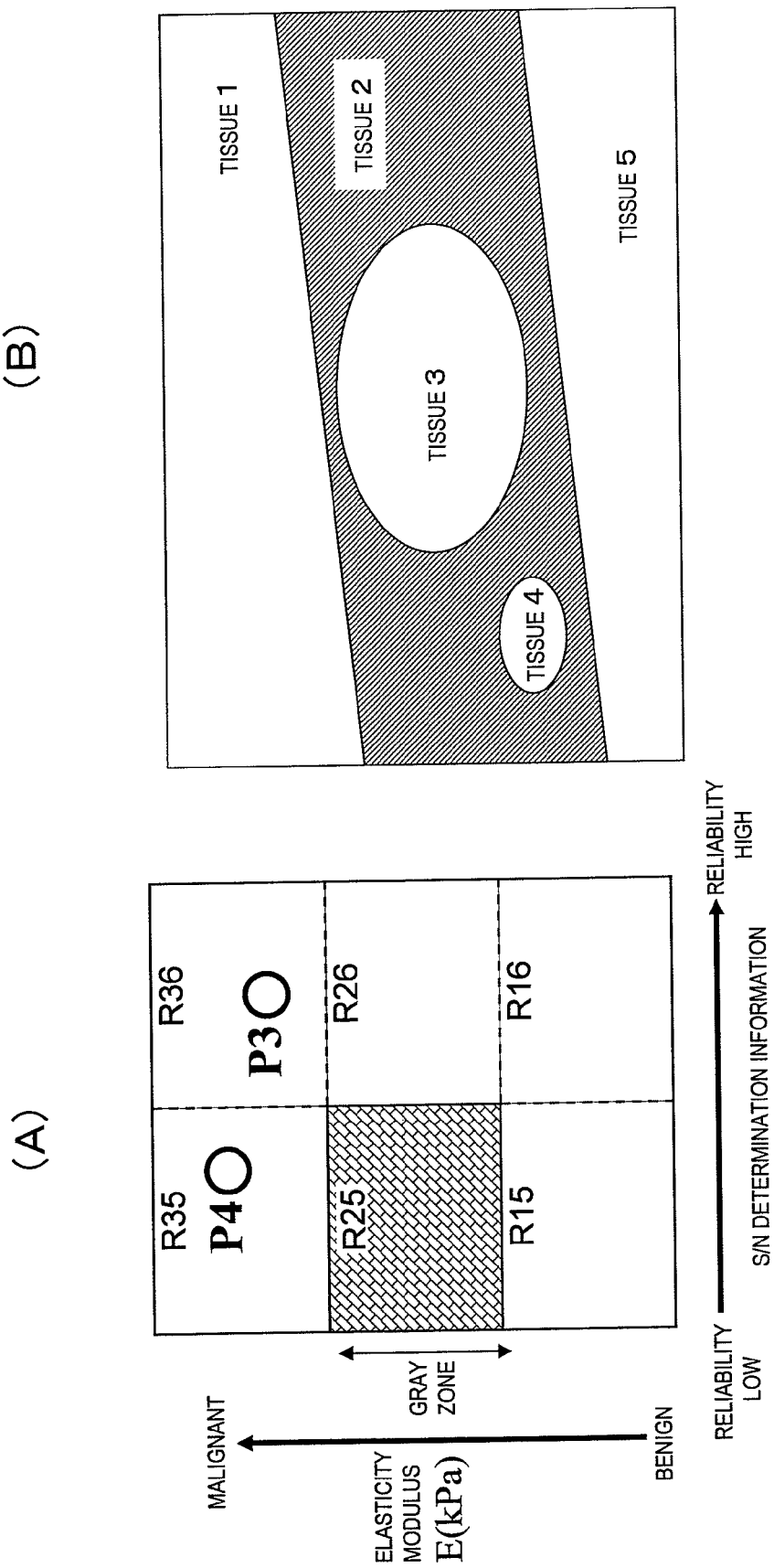

FIG. 6 shows a two-dimensional color map and a color elastic image in practical example 2 of the embodiment 1.

FIG. 7 explains displacement dispersion.

FIG. 8 shows a two-dimensional color map and color elastic image of practical example 3 of the embodiment 1.

FIG. 9 is an explanatory diagram for a practical example of embodiment 2, about construction of a color elastic image wherein a plurality of items of elastic information are converted into a common index value and combined.

Figure 10:
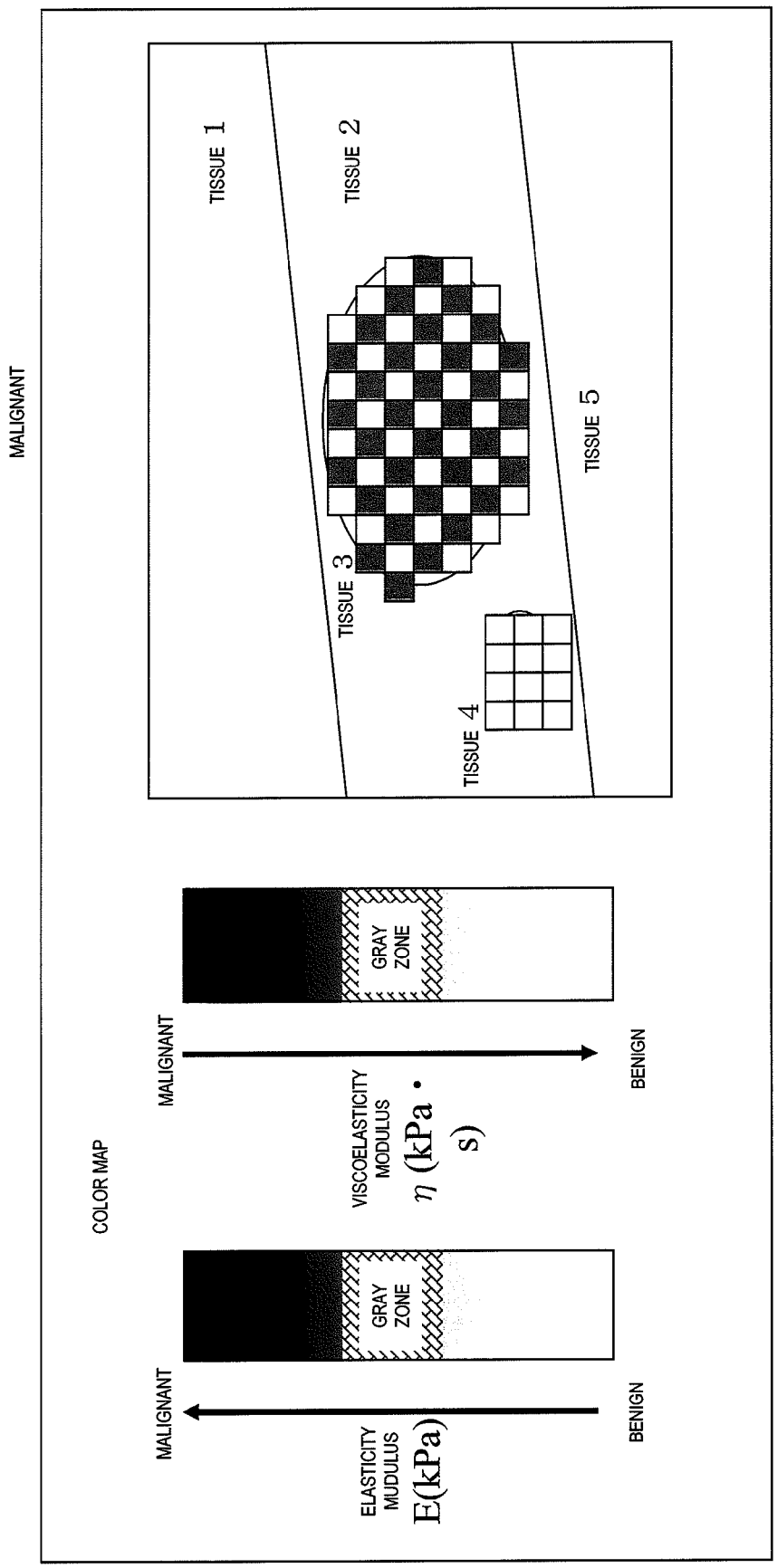

FIG. 10 is an explanatory diagram for a practical example of embodiment 3, about construction of a mosaic-like color elastic image by coloring a plurality of items of elastic information to different one-dimensional color maps and alternately varying the items of elastic information of the adjacent pixel region.

Figure 11:
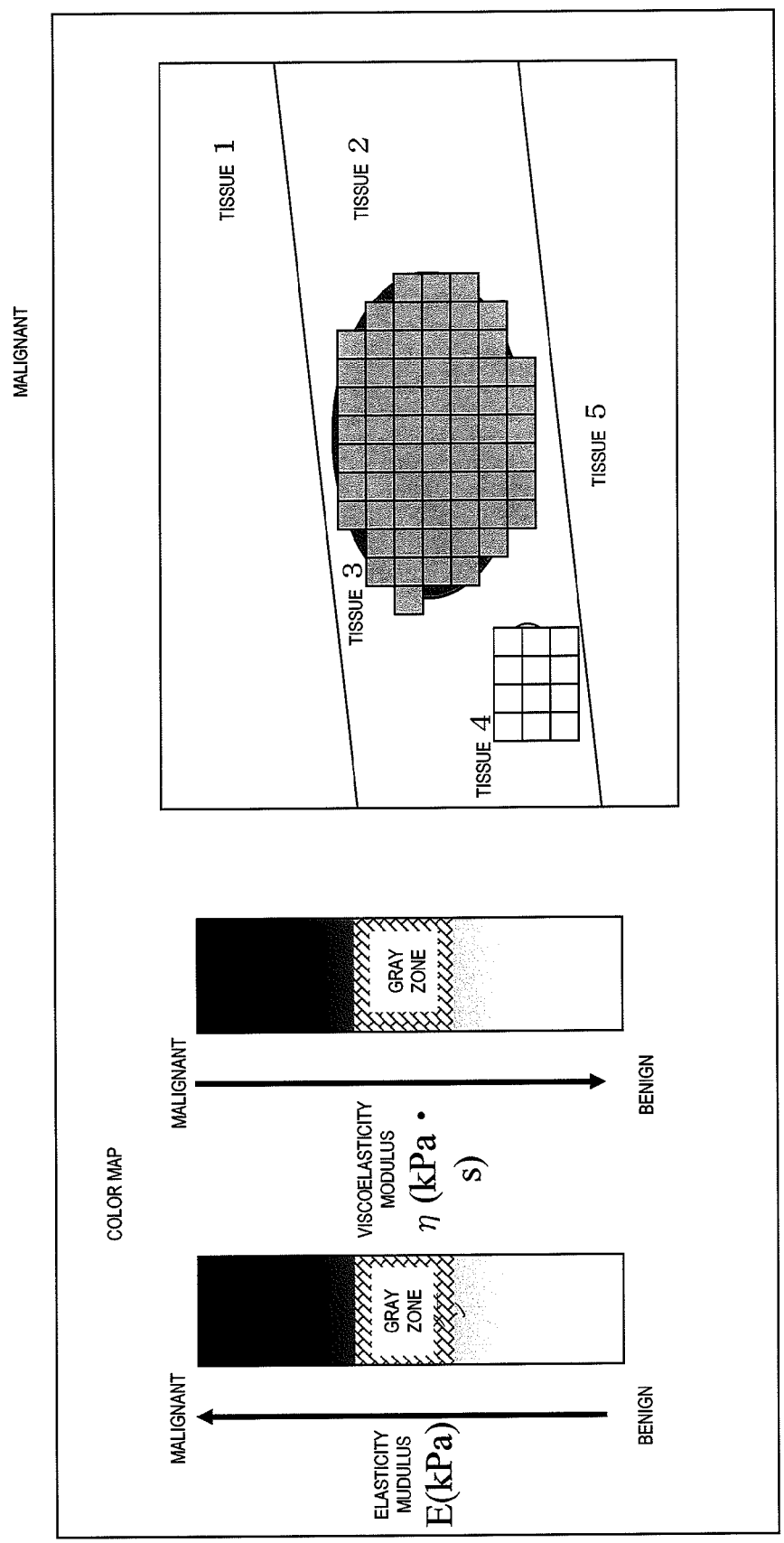

FIG. 11 shows a mosaic-like color elastic image constructed by coloring a plurality of items of elastic information in another practical example of the embodiment 3 by different one-dimensional color maps, and alternately varying the items of elastic information in the adjacent pixel region.

FIG. 12 is an explanatory diagram of embodiment 4 displaying the set plurality of items of elastic information in a target region ROI as numeric values, length of bar charts and a graph of time variation.

BEST MODE FOR CARRYING OUT THE INVENTION

Hereinafter, the elastic image display device and elastic image display method of the present invention will be described based on embodiments.

Embodiment 1

Figure 1:
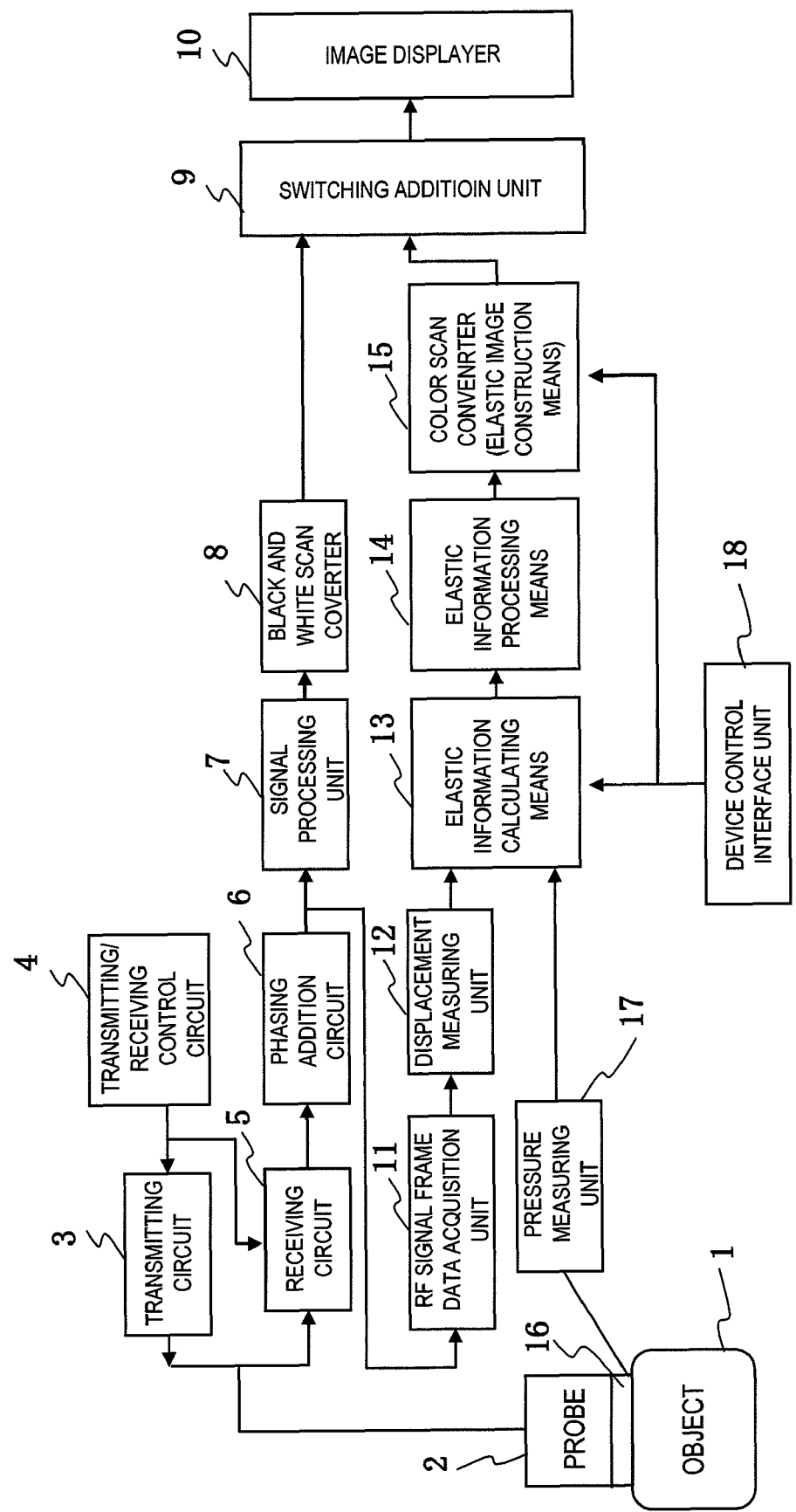
FIG. 1 shows a configuration diagram of an ultrasonic diagnostic apparatus in embodiment 1 for executing the elastic image display method of the present invention.

As an example of the elastic image display device of the present invention, for example, a block configuration diagram of a first embodiment of an ultrasonic diagnostic apparatus will be shown in FIG. 1. As shown in the diagram, an ultrasonic probe 2 for applying to an object 1 is formed having ultrasonic transmission/reception plane in which a plurality of transducers for transmitting/receiving ultrasonic waves to/from the object 1 are arranged. The probe 2 is driven by ultrasonic pulses supplied from a transmission circuit 3. A transmission/reception control circuit 4 controls the timing for transmitting an ultrasonic pulse for driving a plurality of transducers of the probe 2, and forms an ultrasonic beam toward the focal point set in the object 1. Also, the transmission/reception control circuit 4 electronically scans an ultrasonic beam in arrangement direction of the transducers of the probe 2.

On the other hand, the probe 2 receives the reflected echo signals generated from object 1 and outputs them to a reception circuit 5. The reception circuit 5 loads the reflected echo signal in accordance with a timing signal inputted from the transmission/reception control circuit 4 and performs reception process such as amplification. The reflected echo signal performed with receiving process by the reception circuit 5 is amplified by adding phase of the reflected echo signal received by the plurality of transducers in a phasing addition circuit 6. An RF signal of the reflected echo signal phased and added in the phasing addition circuit 6 is inputted to a signal processing unit 7 and performed with signal processing such as gain compensation, log compression, detection, edge enhancement and filtering. The RF signal generated in the phasing addition circuit 6 may be a complex demodulated I,Q signal.

The RF signal processed by the signal processing unit 7 is transmitted to a black and white scan converter 8, converted into a digital signal there and also into a 2-dimensional cross-sectional image data corresponding to a scanned plane of an ultrasonic beam. The above-mentioned signal processing unit 7 and the black and white scan converter 8 constitute image reconstruction means of a cross sectional image (B-mode image). The cross-sectional image data outputted from the black and white scan converter 8 is delivered to an image display 10 via a switching addition unit 9, and the B-mode image is displayed.

On the other hand, the RF signal outputted from the phasing addition circuit 6 is transmitted to an RF signal frame data acquisition unit 11. RF signal frame data acquisition unit 11 acquires the RF signal group corresponding to the scanning plane (cross-section) of the ultrasonic beam for a plurality of frame portions as frame data, and stores them in a device such as a memory. A displacement measuring unit 12 sequentially loads a plurality of pairs of frame data which are acquired at different times and stored in the RF frame data acquisition unit 11, obtains displacement vectors of a plurality of measuring points in the cross-section based on the loaded pair of frame data, and outputs them as displacement frame data to an elastic information calculating unit 13.

The elastic information calculating unit 13 of the present embodiment is configured having:

a strain calculating unit for generating strain frame data by obtaining the strain of the biological tissues in the respective measuring points based on the displacement frame data;

an elasticity modulus calculating unit for generating elasticity modulus frame data by obtaining the elasticity modulus of the biological tissues in the respective measuring points based on the strain frame data; and a relevant elasticity modulus information calculating unit for generating frame data of the relevant elastic information by obtaining elastic information other than the strain or elasticity modulus (hereinafter referred to as relevant elastic information). The frame data of the strain, elasticity modulus and relevant elastic information obtained in the elastic information calculating unit 13 are outputted to an elastic information processing unit 14.

The elastic information processing unit 14 performs, with respect to the frame data of the respective items of elastic information that are inputted from the elastic information calculating unit 13, a variety of image processing such as smoothing process in the coordinate plane, contrast optimization process, smoothing process in the time axis direction among the frames, and outputs the processed frame to a color scan converter 15.

The color scan converter is a part having a function of the composite elastic image construction unit for constructing one elastic image in which a different plurality of items of elastic information relate to the characteristic of the present embodiment are synthesized. It loads the frame data of the elasticity modulus and relevant elastic information being processed by the elastic information processing unit 14, and constructs a color elastic image in which the elasticity modulus and the relevant elastic information are synthesized by appending a hue code for every pixel of the frame data in accordance with the 2-dimensional color map of the set elasticity modulus and the relevant elastic information.

The color elastic image constructed by the color scan converter 15 is to be displayed on the image display 10 via the switching addition unit 9. Also, the switching addition unit 9 is formed having:

a function for inputting a black and white cross-sectional image outputted from the black and white scan converter 8 and a color elastic image outputted from the color scan converter 15 and displaying one of them by switching the images;

a function for displaying one of the images thereof by making it translucent, performing additive synthesis and superimposing onto the image display 10; and a function for juxtaposing and displaying both images. Though not shown in the diagram, it is also capable of calling up past image data and displaying it on the image display 10 according to the command from a device control interface unit 18, by mounting a cine memory unit for storing the image data outputted from the switching addition unit 9.

The basic operation of such configured present embodiment will be described. First, while varying the pressure to be added to the object 1 using the probe 2, an ultrasonic beam is scanned to the object 1 and the reflected echo signal from the scanning plane is continuously received. Then the cross-sectional image is reconstructed by the signal processing unit 7 and the black and white scan converter 8 based on the RF signals outputted from the phasing addition unit 6, and displayed on the image display 10 via the switching addition unit 9.

On the other hand, in the process of varying the pressure to be added to the object 1, the RF signal frame data acquisition unit 11 loads the RF signal, synchronizes it with the frame rate, repeatedly obtaining the frame data, and stores them in the incorporated frame memory in time-series order. Then it continuously selects a plurality of pairs of frame data, having a pair of frame data with different acquisition times as a unit, and outputs them to the displacement measuring unit 12. The displacement measuring unit 12 constructs displacement frame data by performing 1-dimensional or 2-dimensional correlation process on the selected pair of frame data and measuring the displacement of the respective measuring points in the scanning plane. AS for the detection method of this displacement vector, for example, the methods such as the block matching method or the gradient method are known which are disclosed in JP-A-H5-317313. The block matching method divides an image into, for example, blocks formed by N×N pixels, searches for the block which is the most approximated to the target block of the present frame from the previous block, and obtains the displacement of the measuring point based on the searched block. Also, this method is capable of calculating the displacement by performing auto-correlation on the same region of a pair of RF signal frame data.

The displacement frame data obtained in the displacement measuring unit 12 is inputted to an elastic information calculating unit 13. The elastic information calculating unit 13 calculates a plurality of items of elastic information that are set in advance such as strain of each measuring point, elasticity modulus and relevant elastic information, and outputs the necessary elastic information frame data to an elastic information processing unit 14. Calculation of the strain is performed by spatially differentiating the strain, as commonly known. Also, elasticity modulus of the respective measuring points is calculated based on the obtained strain. To obtain the elasticity modulus, the pressure value measured by a pressure measuring unit 17 is loaded, and the stress in the respective measuring points are calculated based on the loaded pressure values. The pressure measuring unit 17 calculates the stress of the measuring point in the object 1 based on the pressure detected by a pressure sensor 16 placed between the ultrasonic transmission/reception plane of the probe 2 and the object 1.

Figure 3:
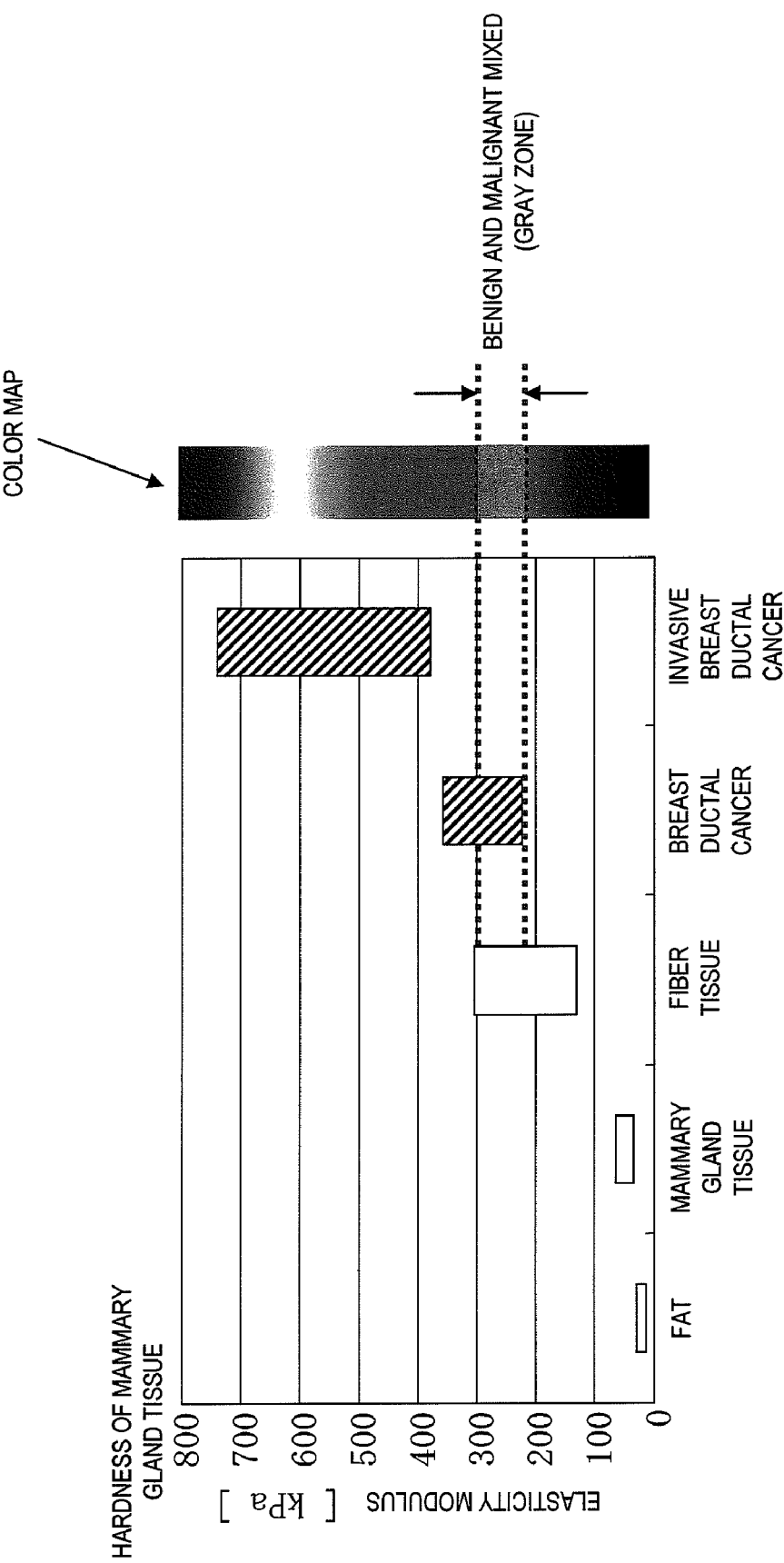
FIG. 3 shows an example of the relationship between elasticity modulus among the respective regions of mammary gland tissues.

The elasticity modulus calculating unit of the elastic information calculating unit 13 calculates the elasticity modulus E (for example, Young's modulus) of the respective measuring points on the scanning plane from the stress in the respective measuring points and the strain frame data obtained in the strain calculating unit of the elastic information calculating unit 13, and outputs them to the elastic information processing unit 14. Here, FIG. 3 shows an example of measuring the elasticity modulus of the respective portions of mammary gland tissues (reference: T. A. Krouskop et. al, Ultrasonic Imaging, 1998). In the diagram, the horizontal axis indicates the respective regions of mammary gland tissues, and the longitudinal axis indicates the elastic modulus [kPa]. As shown in the diagram, the fat and the benign mammary gland tissues has small enough elasticity modulus, and the elasticity modulus of the invasive mammary gland tumor is generally 380~730. On the other hand, benignant fiber tissues generally has elasticity modulus of 130~300, but a part of the mammary gland tumor which is malignant has generally 220~360, and the range of 220~300 where the both regions overlap becomes the gray zone at which the possibility for benignancy and malignancy are mixed. Therefore, if only the elasticity modulus is used as an index, the benignancy and malignancy cannot be differentiated in the region having the elasticity modulus in gray zone.

Given this factor, in this embodiment as will be described later in the respective embodiments, the relevant elastic information that are different from strain and elasticity modulus are obtained in the relevant elastic information calculating unit of the elastic information calculating unit 13 and outputted to the elastic information processing unit 14. As for the elastic information, the information correlated with a variety of elasticity can be applied as described below. The elastic information processing unit 14 performs the processing such as smoothing process on the inputted elasticity modulus and the relevant elastic information, and outputs them to the color scan converter 15.

Figure 2:
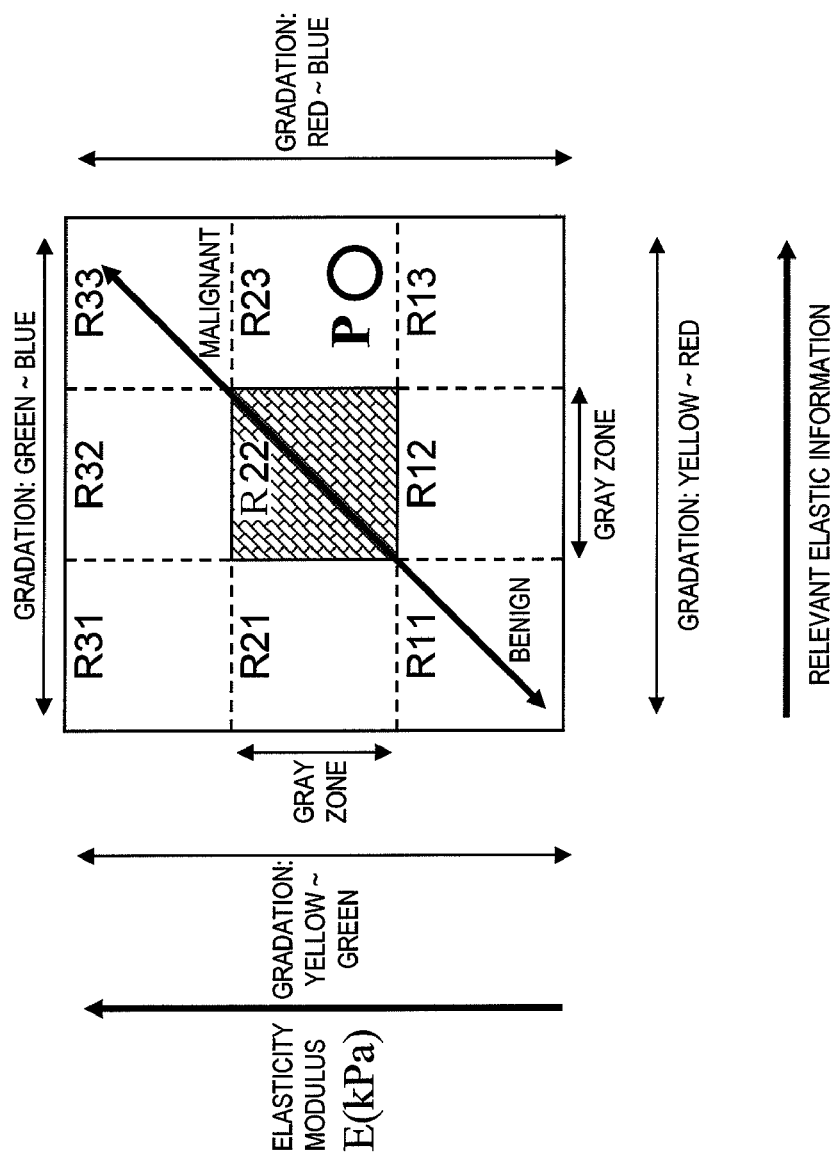
FIG. 2 shows a configuration of a two-dimensional color map for constructing a color elastic image of embodiment 1 related to the present invention.

The color scan converter 15 synthesizes a plurality of different items of elastic information, and constructs one elastic image. A 2-dimensional color map as shown in FIG. 2 is set in the color scan converter 15. It is set so that the longitudinal axis indicates the elasticity modulus E[kPa] and the horizontal axis indicates the relevant elastic information, wherein the elasticity modulus E becomes larger from lower to the upper, that is the longitudinal axis is for differentiating malignancy from benignancy of the biological tissues as moving from lower to the upper. The horizontal axis is set so that the relevant elastic information increases from the left to the right, that is, malignancy can be differentiate from benignancy as moving from the left to the right. Also, hue gradations of, for example, 256 gradations are set along the longitudinal axis and the horizontal axis. Moreover, gradation of hues is respectively set on the left-right axis of the longitudinal axis and the top-bottom axis of the horizontal axis. In the diagram, the gradation from yellow to green is set on the left axis of elasticity modulus, the gradation from red to blue is set on the right axis, the gradation from yellow to red is set on the bottom axis of the relevant elastic information, and the gradation from green to blue is set on the top axis. This means that the gradation is set not only on the longitudinal axis or the horizontal axis but also in arbitrary directions including oblique directions, and the hue allotted on the 2-dimensional plane of a 2-dimensional map has unique hue in all points of the plane.

Therefore, in accordance with the 2-dimensional color map of FIG. 2, as shown by arrows in the diagram, the right upper corner indicates malignancy in both elasticity modulus and the relevant elastic information, and the left lower corner indicates benignancy in both elasticity modulus and the relevant elastic information. Also, the gray zones of the elasticity modulus that E are difficult to differentiate benignancy or malignancy are regions R21, R22 and R23, and the gray zones of the relevant elastic information are R12, R22 and R32. However, if evaluation of both elasticity modulus and relevant elastic information are considered, the regions R21 and R12 are differentiated as having high possibility of benignancy and the regions R23 and R32 are differentiated as having high possibility of malignancy, thus the gray zone can be narrowed down to the region R22.

Here, in the color scan converter 15, the procedure for constructing a color elastic image in which two items of elastic information that are elasticity modulus and the relevant elastic information are synthesized will be described using the 2-dimensional color map in FIG. 2. The color scan converter 15 constructs a color elastic image by loading the frame data of the elasticity modulus and the relevant elastic information on which the processing such as smoothing is performed by the elastic information processing unit 14, reading the hue code of the position where the elastic modulus and the relevant elastic information of the frame data intersect for each pixel unit on the 2-dimensional color map, and setting the hue code as the hue of the respective pixels corresponding to the respective measuring points.

As mentioned above, in accordance with the present embodiment, the gray zones that are difficult to be differentiated by one item of elastic information can be considerably reduced, by considering the relevant elastic information. As a result, it is possible to improve the differentiation accuracy of benignancy and malignancy of the gray zone that has been difficult to differentiate only by elasticity modulus.

Also, in place of the color scan converter 15, the black and white scan converter can be used. In this case, the differentiation of benignancy and malignancy can be performed, by setting the bright luminance for the region having large elasticity modulus and the relevant elastic information, and setting the dark luminance for the region having small elasticity modulus and the relevant elastic information.

Hereinafter, detailed configuration and operation of the elastic information calculating unit 13 and the color scan converter 15 that are the main feature of the present embodiment will be described based on the concrete example of the relevant elastic information.

Practical Example 1

As the relevant elastic information of the present invention, embodiment 1 to which the non-linear parameter for representing the nonlinearity of elastic modulus with respect to the strain amount is applied will be described. A relevant elastic information calculating unit by which the elastic information calculating unit 13 of the present embodiment is configured obtains non-linear parameter α which represents the nonlinearity as the elastic feature of the biological tissues in the target region, as shown in the 2-dimensional color map in FIG. 4 (A).

More specifically, as shown in FIG. 5, while the biological tissues generally have the characteristic that they harden more as the pressure or strain amount of compression increases and fatty tissues exhibit linearity wherein the approximately constant elasticity modulus is measured up to the range of large strain amount, fiber tissues and invasive tumors show the phenomenon of strain hardening due to drastic increase of elasticity along with the increase of the stain amount. Also, invasive malignant tumors have a larger degree of strain hardening than the fiber tissues, and larger nonlinear parameter to be described later. Here, the strain amount is an integration value of the strain from start of pressure to the measuring point, and is used being distinguished from the strain of the strain frame data.

As shown in FIG. 5, the relationship between the strain amount of biological tissues Σε[%] and elastic modulus E[kPa] generally indicates non-linear elastic response. Given this factor, the strain amount from the start of pressure to the measuring point is obtained based on the above-mentioned strain frame data, and the relationship data between the strain amount and the elasticity modulus. Then it is suggested to approximate the nonlinear curve of the strain amount—elasticity modulus using a function, obtain non-linear parameter α based on the most approximated curve using the method such as least-squares method, and evaluate the obtained parameter as the information representing the nonlinearity of the tissues (for example, Journal of Electronic Information Communication Institute, 2001/12 Vol. J84-A No. 12, "Imaging of Non-linear Character of Tissues by Ultrasonic Waves" by Nitta, et al.).

However, in the case that nonlinearity is noticeable in the actual tissues, since the conventional means had been using the Young's modulus as elasticity modulus E and the slope of the curve representing the relationship of the elasticity modulus E with respect to the strain amount Σε is assumed by one-dimensional parameter, the information to be obtained cannot be quantitative thus not sufficient to be applied to the conclusive diagnosis.

Given this factor, in the present embodiment, the higher-order function shown in the following formula (1) is to be applied as a curve in which the nonlinearity response of the tissues is faithfully approximated.

$$E=E0+\alpha\times(\Sigma\epsilon)^\gamma \quad (\gamma \text{ is the whole number of 2 or more}) \quad (1)$$

Since the non-linear parameter α of formula (1) is the value equivalent to the slope variation of the curve, the value increases as the nonlinearity of the tissues increases, and the value gets closer to zero as the curve gets closer to a straight line. The formula (1) can be further generalized, and approximated by the exponential function type using the following formula (2). Also, it is possible to set non-linear parameter α for representing the nonlinearity.

$$E=(E0-1)+\exp(\alpha\times\Sigma\epsilon) \quad (2)$$

In accordance with the approximate function shown in formula (1) or (2), it is possible to perform a quantitative evaluation by obtaining highly accurate and defined non-linear parameter α despite of the degree of compression, even in the case of evaluating non-linear parameter α in arbitrary measuring zones. In other words, even when the relationship between the strain amount and elasticity modulus (Σε(0), Y(0)) measured in the present time t(0) and the relationship between the strain amount and elasticity modulus (Σε(−1), Y(−1)), (Σε(−2), Y(−2)), . . . obtained in the past time t(−1), t(−2), . . . are applied as accumulated data of relationship between the strain amount and elasticity modulus, and the non-linear parameter α is evaluated in real time in the present time t(0), a numerical information and image information of the non-linear parameter thereof turn out to be objective, without depending on the degree of compression.

Therefore, it is possible to display non-linear parameter α as an elastic image in real time, and benignancy and malignancy of tissues can be differentiated with high accuracy by synthesizing the elastic images of non-linear parameter α, even in the gray zone where differentiation of benignancy and malignancy is uncertain.

FIG. 4 shows an example of a color elastic image constructed by the present embodiment. FIG. 4 (A) is a setting example of a 2-dimensional color map, and FIG. 4 (B) is a color elastic image constructed using the 2-dimensional color map thereof. As shown in FIG. 4 (A), in the 2-dimensional color map, elasticity modulus E[kPa] is allotted to the longitudinal axis and non-linear parameter α is allotted to the horizontal axis. Also, hue gradation for the longitudinal axis and the horizontal axis are set in the same manner as FIG. 2.

FIG. 4 (B) is an example of a color elastic image in which the both items of elastic information that are elastic modulus and non-linear parameter are synthesized in the color scan converter 15 using the above-mentioned 2-dimensional color map. In the same diagram, since a hue of the position in P3 on the 2-dimensional color map is allotted to a tissue 3 whose elasticity modulus E is high and non-linear parameter α is also high, malignancy can be strongly suspected. On the other hand, tissue 4 is allotted with a hue of the position of P4 and its elasticity modulus E has a value in the gray zone but non-linear parameter α is sufficiently large, thus malignancy is suspected more strongly than benignancy. The other tissues 1,2 and 5 are to be determined as benign.

As described above, in accordance with the present embodiment, accuracy for differentiating benignancy or malignancy can be improved, since the gray zone wherein one item of elastic information could not differentiate can be sufficiently reduced. Moreover, there is no need to compare two images of elastic image and non-linear parameter image, and accuracy for differentiating benignancy or malignancy by one image can be improved, visibility and examination efficiency are also improved.

Practical Example 2

FIG. 6 (A) shows a 2-dimensional color map of embodiment to which S/N determination information related to the reliability of calculation result as relevant elastic information other than elasticity modulus E is applied, and FIG. 6 (B) shows an example of the color elastic image wherein the images are synthesized based on the two items of elastic information that are the elastic modulus and S/N determination information.

A relevant elastic information calculating unit of an elastic information calculating unit 13 in the present embodiment comprises an S/N determination information calculating unit. The S/N determination information calculating unit is for acquiring S/N determination information represented by local dispersion (variance) of displacement distribution included in the calculation result of the displacement or coefficient of correlation obtained by displacement calculation of the displacement measuring unit 12.

The displacement frame data acquired in the displacement measuring unit 12 is denoted by 2-dimensional displacement vector (Xi,j,Yi,j) in each measuring point, as shown in FIGS. 7 (A) and (B). That is, element data groups of the components in the vertical direction of the image (y-direction) and components in the lateral direction of the image (x-direction) are represented respectively as:

$$X_{i,j}(t)\ (i=1, 2, 3, \ldots, N, j=1, 2, 3, \ldots M)$$

$$Y_{i,j}(t)\ (i=1, 2, 3, \ldots, N, j=1, 2, 3, \ldots M).$$

The subscrip "i" denotes the coordinate in the lateral direction, and "j" denotes the coordinate in the vertical direction. The S/N determination information calculating unit generates, for example, the frame data of displacement dispersion which is one of the items of S/N determination information and the feature of the present embodiment, based on the displacement frame data in FIG. 7.

Dynamic motion of tissues of the respective regions in human body when unidirectional pressure is added to the object 1 has significant difference in compliance with the type of tissues such as: (A) very hard solid tissues (for example, cancer tumor), (B) soft solid tissues (for example, fiber adenoma) or (c) fluid cystic tissues (for example, a cyst). For example, the tissues of type (A) forming cancer tumor, etc. tend to have the same motion in a cluster due to high density and high degree of tissue binding. On the contrary, the tissues around the cancer tumor, etc. have dispersion in size or direction of the motion compared to the cancer tumor, etc. due to lower degree of tissue binding.

By evaluating the above-described difference of dynamic motion of tissues as the degree of displacement dispersion, it is possible to distinguish the cancer tumor, etc. or differentiate the size thereof. Also, in the case of (B) which is comparatively soft tissues such as fiber adenoma, the above-described differentiation can be made when they are compressed, size and direction of the displacement is dispersed depending on the compressed position and the slopes are generated in the dispersion with respect to the compression direction, by the degree of slope generated in the dispersion which becomes larger as being farther from the center of the compression. Further, in the case of (C) noncellular tissues such as cysts, variation of the displacement has distinct dispersion in size and direction of the displacement, since there is no binding of tissues and motion of the respective regions are entirely free. Given this factor, in displacement dispersion calculating unit, the displacement dispersion frame data is to be generated as the relevant elastic information by calculating the displacement dispersion indicating the size and direction of the displacement in the respective measuring points.

Also, since displacement is correlated with the degree of pressure, there are occasions that the displacement dispersion of the same tissues indicating size and direction of the displacement are erroneously recognized as information of the different tissues. Given this factor, in order to express the size and direction of the displacement in quantitative values, it is desirable to obtain the degree of displacement dispersion by normalizing the average value of the plurality of displacements included in the local region surrounding the respective measuring points. By doing so, binding relationship between the target region and the surrounding tissues can be objectively and quantitatively evaluated, and new elastic information can be attained, for example, for easily differentiating the tissue characterization such as whether the tissues are solid or cystic. Since degree of displacement dispersion is the normalized local displacement dispersion, the tissue characterization can be evaluated quantitatively without depending on the pressing direction. Also, in the measuring point wherein the reciprocal number of the displacement dispersion as S/N determination information (since the reliability gets lower as the displacement dispersion gets larger) is smaller than a certain set threshold value, it is determined that noise is included in the displacement calculation of the measuring point thereof due to a certain reason such as the case that the cross-section of the measuring point is displaced before/after the compression, the elasticity modulus using the displacement data or the other elastic data can be set down as possessing lower reliability.

The S/N determination information calculating unit can calculate coefficient of correlation that is another example of S/N determination information, in place of displacement dispersion. This coefficient of correlation is a coefficient obtained in the case of calculating displacement distribution using a correlation method. Procedure of calculating the displacement distribution by correlation method is to set a template using the RF signal waveform of the tissue region before the compression and to search for the region having the most approximated waveform of the set template using the RF signal after the compression. Then the point calculated with the largest coefficient of correlation in the set search range is recognized as the destination of the template after the compression, and the displacement is obtained. Therefore, the absolute value of the coefficient of correlation is the value representing the degree of matching of the templates, which gets closer to "1" as the reliability of the displacement calculation gets higher, and gets closer to "0" as the reliability gets lower. Given this factor, the measuring point wherein the coefficient of correlation does not surpass the set threshold (for example, 0.8) is determined that a noise is included in displacement calculation of the measuring point thereof for some reason, and the elasticity modulus using the displacement data or other elastic data are set down as possessing lower reliability.

FIGS. 6 (A) and (B) show examples for generating a color elastic image by setting a 2-dimensional color map having two axes which are the elastic modulus and the S/N determination information, using (the reciprocal number of) displacement dispersion the S/N determination information based on the coefficient of correlation as a scale of reliability. As shown in FIG. 6 (A), the 2-dimensional color map of the present embodiment has the size of elastic modulus as a longitudinal axis, and the reliability of the elasticity modulus based on the S/N determination information as a horizontal axis. The elastic modulus is set in the same manner as FIG. 2, and the S/N determination information possess higher reliability as it shifts more toward the right. Also, regions R25 and R26 are the gray zone of the elasticity modulus, and R15, R25 and R35 are the gray zone of the S/N determination information. However, the region R26 does not have to be evaluated as the gray zone of the elasticity modulus since it possesses higher reliability based on the S/N determination information.

For example, as shown in FIG. 6 (B), the tissue 3 is appended with a hue of the position of P3 on the 2-dimensional color map, having high elasticity modulus E and high reliability of S/N determination information, thus malignancy can be strongly suspected. On the other hand, tissue 4 is appended with a hue of the position of P4 since it has high elasticity modulus at the same level as the tissue 3 but has low reliability of the S/N determination information, and the elasticity modulus E is suspect in its reliability though not in the gray zone, thus the re-examination is to be encouraged.

In accordance with the present embodiment, as embodiment 1, the gray zone wherein the differentiation could not be performed by one item of elastic information can be sufficiently reduced, whereby it is possible to improve the accuracy of determining benignancy or malignancy. Visibility and examination efficiency can be particularly improved since differentiation of benignancy or malignancy can be performed with high accuracy by one elastic image, without comparing two images of an elastic image and an image containing S/N determination information.

Practical Example 3

FIG. 8 (A) shows a 2-dimensional color map of embodiment 3 to which an angle with respect to the compressing direction as the relevant elastic information is applied other than elasticity modulus E, and FIG. 8 (B) shows a diagram explaining the angle with respect to the compressing direction. As shown in FIG. 8 (B), directly underneath the probe to which the pressure is applied (compressing direction) will receive an adequate compression. However, since the position deviated from the compressing direction by θ degrees will not receive the adequate compression, it is assumed that the elastic information based on the displacement measuring data of the position thereof is not quite accurate. Especially, since the column-shaped probe having large curvature is used for examining prostate cancer, it is difficult to apply the same amount of pressure in all directions. Consequently, there are regions having adequate compression and regions where the compression is not adequately applied in the same measuring cross-section.

Given this factor, the 2-dimensional color map of the present embodiment sets the longitudinal axis as the size of elasticity modulus and the horizontal axis as an angle θ ($-\pi/2 \sim +\pi/2$) with respect to the pressure direction. By such setting, it is possible to plainly evaluate the accuracy of pressure condition under which the measurement result is taken with respect to the elasticity modulus value in the target region.

Thus the elasticity modulus measured in the range of inadequate angle θ has a low accuracy, and a reexamination should be induced. In concrete terms, the tissues in a region R32 to which the hue of P3 is appended is obvious that the elasticity modulus is measured under adequate compression condition. On the contrary, it can be recognized that the tissues in a region R33 to which the hue of P4 is appended is the value being measured under inadequate compression condition, though it has high elasticity modulus that indicates malignancy. Therefore, while observing the color image of the present example, as for the target region to which the hue of the region of R33 is appended when the color image of the present embodiment is observed, it is possible to differentiate benignancy and malignancy under adequate compression in real time by applying compression again toward the target region.

Consequently, the same effect can be achieved as practical examples 1 and 2 in accordance with the present example.

Practical Example 4

While the above practical examples 1~3 are for constructing color elastic images in which two items of elastic information are combined, using a 2-dimensional color map of elasticity modulus—non-linear parameter α, elasticity modulus—S/N determination information and elasticity modulus—compression direction respectively, the present invention is not limited to them. For example, a 2-dimensional color map can be set by calculating, combining with elasticity modulus, elastic information such as viscoelasticity modulus, displacement, stress, strain Poisson's ratio and strain ratio between two target regions, which achieves the same effect as the practical examples 1~3.

Also, the combination does not have to be made with elasticity modulus, but the above-mentioned items of elastic information can be arbitrarily combined in order to achieve the same effect as the practical examples 1~3.

Embodiment 2

While the present invention for constructing color elastic images in which two items of elastic information are synthesized using a 2-dimensional color map in the above-mentioned embodiment 1, the present invention is not limited thereto. More specifically, one color elastic image can be constructed by generating frame data through calculating a plurality of different items of elastic information in the elastic information calculating unit 13 of FIG. 1 and superimposing those frame data of elastic information in color scan converter 15.

In accordance with the present embodiment, as is in embodiment 1, accuracy of differentiation between benignancy and malignancy can be improved since gray zones where differentiation cannot be made by one item of elastic information can be substantially reduced. Especially, visibility and examination efficacy can be improved since accuracy of differentiation of benignancy and malignancy can be made by one elastic image without comparing two images between an image of elasticity modulus and an image of another item of elastic information.

An example of a color elastic image constructed by applying embodiment 2 will be described using FIG. 9. The present embodiment calculates frame data of a plurality of items of elastic information such as elasticity modulus, viscoelasticity modulus and non-linear parameter in the elastic information calculating unit 13, and obtains probability of malignancy in tissues (grade of malignancy) for each measuring point of the frame data in the respective items of elastic information. Here, the viscoelasticity modulus is the elasticity modulus considering the time that the biological tissues on which the pressure is added revert back to the original condition. The FIGS. 9 (A)~(C) indicate such examples of malignancy probability image using elasticity modulus, malignancy probability image using viscoelasticity modulus and malignancy probability image using non-linear parameter respectively. Then a malignancy probability Pij(x) is obtained for each measuring point (i,j) of a plurality of malignancy probability images x (here, x=1, 2, 3, . . . ). Here, i=1, 2, 3, . . . , N and j=1, 2, 3, . . . M.

Further, multiplication of malignancy probability Pij(x) of a plurality of malignancy probability images are obtained for each measuring pint (i,j) as malignancy probability Pij by comprehensive diagnosis using the following formula:

$$Pij = Pij(1) \times Pij(2) \times Pij(3) \times \ldots$$

By setting the obtained value Pij(x) as a pixel value and appending the hue which is set to the color bar indicated on the left side in FIG. 9, the color elastic image shown in FIG. 9 (D) is constructed.

In accordance with the present embodiment, the gray zone where differentiation could not be made by only one elastic image can be substantially reduced, since a plurality of different items of elastic information is converted into an evaluated value indicating the evaluation of malignancy, and an elastic image is synthesized by allocating the hue (or luminance) of the respective pixels according to the evaluated value of each item of elastic information. As a result, accuracy in differentiation of benignancy and malignance can be improved. Particularly, visibility and examination efficacy can be improved since there is no need to compare a plurality of elastic images and differentiation can be effectively made between benignancy and malignancy by one color elastic image.

While the example for obtaining the multiplication of malignancy probability Pij(x) for each measuring point (i,j) and setting the obtained multiplication as a pixel value is described in the present embodiment, the malignancy probability Pij obtained by the following formula can be set as an index in place of the previously mentioned multiplication of malignancy probability, by setting malignancy probability Pij as the length of multidimensional vector.

$$Pij = \sqrt{(Pij(1) \times Pij(1) + Pij(2) \times Pij(2) + Pij(3) \times Pij(3) \times \ldots)}$$

Further, instead, the malignancy probability Pij can be set as the average value of the malignancy probability Pij(x) as shown in the following formula.

$$Pij = (Pij(1) + Pij(2) + Pij(3) + \ldots) / (\text{number of elastic images})$$

Embodiment 3

While the present invention for constructing a color elastic image in which two items of elastic information are synthesized using a 2-dimensional color map is described in the embodiment 1, in the present embodiment, one-dimensional color map is set for each item of elastic information, and gradation of the hues that are not compatible with each other and mutually exclusive are set, for example, warm color group and cold color group, to the two color maps. This means is characterized in that the two color maps are alternately colored by pixel unit or adjacent plurality of pixel group unit, and a mosaic-like color elastic image is synthesized.

FIG. 10 is an example of a mosaic-like color elastic image constructed by the present embodiment. As shown in the diagram, one-dimensional color map is set for each elasticity modulus E[kPa] and viscoelasticity modulus η[kPa?s]. Those color maps are arranged to vary from benignancy to malignancy as it shifts from the bottom toward the top, and the gradation of hues that are not compatible with each other and mutually exclusive are set, for example, warm color group and cold color group, though not visible in the diagram. Also, the vicinity of the intermediate value of those color maps becomes a gray zone that is difficult to differentiate benignancy and malignancy.

By using such color maps, the color elastic image on the right side of FIG. 10 is constructed by synthesizing mosaic-like color elastic images to which the two color maps are alternately colored, for example, by adjacent plurality of pixel group unit. As is apparent from the diagram, a tissue 3 is displayed with mosaic-like hues representing malignancy of elasticity modulus and viscoelasticity modulus, since malignancy is strongly doubted in elasticity modulus and viscoelasticity modulus. On the other hand, a tissue 4 is in a gray zone region that is difficult to diagnose, but strong doubt of malignancy can be recognized in viscoelasticity modulus.

FIG. 11 shows another example of mosaic-like color elastic image constructed by the present embodiment. As shown in the diagram, the point that one-dimensional color map is set for every elasticity modulus E[kPa] and viscoelasticity modulus η[kPa?s] is the same as FIG. 10. However, those color maps are set, for example, by setting the same color (for example, yellow) for the benignancy direction, and allocating for the malignancy direction the hues that is incompatible with the hues for the benignancy direction so as to differentiate the one from another. Though not visible in the diagram, gradation is set in the hues thereof. Also, the vicinity of the intermediate value of those color maps becomes a gray zone that is difficult to differentiate benignancy and malignancy.

When such color maps are used and the mosaic-like color elastic images are synthesized through, for example, alternately coloring by two color maps by a plurality of adjacent pixel group unit, the color elastic image as shown on the right side in FIG. 11 is constructed. As being apparent from the diagram, since mosaic pattern of the region in tissue 4 has yellow color and does not have so much difference in hues, benignancy can be instantly recognized both in elasticity modulus and viscoelasticity modulus. Also, since tissue 3 has mosaic pattern having significantly different colors in the adjacent pixel groups, it is recognizable through comprehensive judgment that malignancy should be strongly doubted.

Embodiment 4

In the above-described embodiment 1, the example for constructing one elastic image by synthesizing two items of elastic information using 2-dimensional color maps is described. The example for constructing one color elastic image by superimposing frame data of a plurality of different items of elasticity information is described in the embodiment 2, and the example for setting a one-dimensional color map for each item of elastic information and synthesizing mosaic-like color elastic images by alternately coloring by pixel unit or by adjacent plurality of pixel group unit is described in the practical example 3.

However, the elastic image display method of the present invention is not limited to the above-described examples, and includes also a practical example 4 for synthesizing the color elastic images shown in FIG. 12. That is, as shown in the diagram, the present embodiment is an example for setting a region of interest ROI in one elastic image or B-mode cross-sectional image, and displaying, for example, the average value of the plurality of items of elastic information in the ROI thereof in forms of numeric numbers, bar charts or time variation graphs. In the diagram, the average value of the elasticity modulus and viscoelasticity modulus in the ROI being set in the tissue 3 is calculated, and those values are displayed in real time in forms of numerical values, bar chart length and time variation graph. Also, to the display images such as elastic images are appended with the hues in accordance with the items of elastic information such as elasticity modulus.

In accordance with the present example, since a plurality of different items of elastic information in the target region is converted into estimated values of malignancy and displayed by contradistinguishing the evaluated values of the plurality of items of elastic information using a bar chart, differentiation of benignancy and malignancy can be performed with high accuracy by instantly comparing a plurality of items of elastic information. It is the same also in the case of comparing a plurality of different items of elastic information in the same target region by at least one of the numeric values, line maps or diagrams.

While the present invention is described above in the embodiments 1~4, the elastic image display method of the present invention is not limited to those examples, and images such as B-mode image, magnetic resonance (MR) image, CT image, blood flow color Doppler image and tissue Doppler image can be applied as other items of elastic information to combined with elasticity modulus, etc. B-mode images or MR images can be used as elastic information since the regions having high elasticity are displayed, for example, in dark colors. Also, blood flow Doppler images can be used for elastic information indicating blood flow information, since malignant tumors (cancer cells, etc.) have high density in a blood vessel. Tissue Doppler images can be used as elastic information upon diagnosing elasticity of muscles such as myocardium.

The present invention is not limited to be executed only on an ultrasonic diagnostic apparatus, but can be executed also on CT or MRI apparatuses. Further, it may be executed on a personal computer, separating off from those diagnostic apparatuses.

Also, while a 2-dimensional color map is exemplified, the present invention can be executed by selecting three (or more than 3) items from elasticity modulus, viscoelasticity modulus, non-linear parameter related to nonlinearity of elasticity modulus with respect to the strain amount, S/N determination information related to the reliability of displacement calculation result, direction of the compression being added to each measuring point, displacement, stress, strain and Poisson's rate, etc. and creating 3-dimensional (or higher-dimensional) color maps. As the items of information to select from are increased, the more gray zones are reduced.

DESCRIPTION OF SYMBOLS

1 . . . object, 2 . . . probe, 3 . . . transmission circuit, 4 . . . transmission/reception control circuit, 5 . . . reception circuit, 6 . . . phasing addition circuit, 7 . . . signal processing unit, 8 . . . black and white scan converter, 9 . . . switching addition unit, 10 . . . image displayer, 11 . . . RF signal frame data acquisition unit, 12 . . . displacement measuring unit, 13 . . .

elastic information calculating unit, 15 . . . color scan converter, 16 . . . pressure sensor, 17 . . . pressure measuring unit.

The invention claimed is:

1. An elastic image display method for obtaining frame data of receiving signals acquired from an object to be examined, comprising the steps of:
    obtaining displacement in a plurality of measuring points based on a pair of frame data having different acquisition times;
    obtaining a plurality of different items of elastic information based on displacement of the respective measuring points; and
    constructing one elastic image based on the obtained plurality of items of elastic information and displaying on the display screen,
    wherein the one elastic image is constructed by allocating hue or luminance of each pixel in compliance with the two items of elastic information based on a two-dimensional map having two items of the elastic information as longitudinal axis and horizontal axis.

2. The elastic image display method according to claim 1, wherein the plurality of items of elastic information are at least two to be selected from elasticity modulus, viscoelasticity modulus, non-linear parameter related to the nonlinearity of elasticity modulus with respect to the strain amount, local dispersion included in calculation result of the displacement or S/N determination information related to reliability of the calculation result of coefficient of correlation, etc., direction of pressure to be added to the respective measuring points, displacement, stress, strain and Poisson's ratio.

3. The elastic image display method according to claim 1, wherein the 2-dimensional map is a 2-dimensional color map, and gradation of different hues are set respectively to the left-right axis of the longitudinal axis and the top-bottom axis of the horizontal axis.

4. The elastic image display method according to claim 3, wherein the item of elastic information of the longitudinal axis is elasticity modulus, and the item of elastic information of the horizontal axis is non-linear parameter related to the nonlinearity of elasticity modulus with respect to the strain amount.

5. The elastic image display method according to claim 3, wherein the item of elastic information of the longitudinal axis is elasticity modulus, and the item of elastic information of the horizontal axis is viscoelasticity modulus.

6. The elastic image display method according to claim 3, wherein the item of elastic information of the longitudinal axis is elasticity modulus, and the item of elastic information of the horizontal axis is the direction of compression being added to each measuring point.

7. The elastic image display method according to claim 1, wherein the one elastic image is constructed by dividing each measuring point into a plurality of setting regions having adjacent plurality of measuring points, obtaining a central value of two items of the elasticity information in each setting region, coloring each pixel of the respective setting regions in accordance with two one-dimensional color maps to which two different hues are respectively allocated with respect to the two items of elastic information.

8. The elastic image display method according to claim 7, wherein the two items of elastic information are elasticity modulus and viscoelasticity modulus.

9. The elastic image display method according to claim 1, wherein the one elastic image is constructed by converting the different plurality of items of elastic image into an evaluated value for evaluating malignancy, and allocating hue or luminance of each pixel to the evaluated value of the respective items of elastic information.

10. The elastic image display method according to claim 1, wherein the one elastic image is an elastic image represented by comparing the different plurality of items of elastic information in the same set target region using at least one of numerical values, line maps and diagrams.

11. The elastic image display method according to claim 10, wherein the one elastic image is an image in which the different plurality of items of elastic information in a target region is converted into an evaluated value of malignancy, and is displayed by comparing the evaluated values of the plurality of items of elastic information using bar charts.

12. The elastic image display method according to claim 10, wherein the one elastic image is an image wherein time variation of the different plurality of items of elastic information in the target region are displayed using a line map so as to compare them.

13. An elastic image display device comprising:
    frame data acquisition means for acquiring frame data of receiving signals obtained from an object to be examined, in the process that the compression to be added to the object is varied;
    displacement measuring means for obtaining displacement in a plurality of measuring points of the scanning plane based on the pair of frame data having different acquisition times;
    elastic information calculating means for obtaining different plurality of items of elastic information in the respective measuring points based on displacement of the respective measuring points;
    elastic image constructing means for constructing one elastic image based on the obtained plurality of items of elastic information; and
    display means for displaying the constructed image,
    wherein the one elastic image is constructed by allocating hue or luminance of each pixel in compliance with the two items of elastic information based on a two-dimensional map having two items of the elastic information as longitudinal axis and horizontal axis.

14. The elastic image display device according to claim 13, wherein the plurality of items of elastic information is to be selected from at least two of elasticity modulus, viscoelasticity modulus, non-linear parameter related to nonlinearity of elasticity modulus with respect to the strain amount, local dispersion included in calculation result of the displacement or S/N determination information related to reliability of the calculation result of coefficient of correlation, etc., direction of the compression being added to the respective measuring points, displacement, stress, strain and Poisson's ratio.

15. The elastic image display device according to claim 13, wherein:
    the 2-dimensional map is a 2-dimensional color map; and
    gradation of different hues are respectively set to the left-right axis of the longitudinal axis and the top-bottom axis of the horizontal axis.

16. The elastic information display device according to claim 13, wherein:
    the elastic information of the longitudinal axis is elasticity modulus; and
    the elastic information of the horizontal axis is non-linear parameter related to nonlinearity of the elasticity modulus with respect to the strain amount.

17. The elastic image display device according to claim 13, wherein:

the elastic information of the longitudinal axis is elasticity modulus; and the elastic information of the horizontal axis is viscoelasticity modulus.

18. The elastic image display device according to claim 13, wherein:

the elastic information of the longitudinal axis is elasticity modulus; and the elastic information of the horizontal axis is compression direction added to the respective measuring points.

19. The elastic image display device according to claim 13, wherein the elastic image constructing means constructs the one elastic image by dividing measuring points of a tissue image into a plurality of setting regions having adjacent plurality of measuring points, acquiring a center value of the two items of elastic information in the respective setting regions, and coloring each pixel of the respective setting regions in compliance with the two one-dimensional color maps to which two different hues are respectively allocated with respect to the two items of elastic information.

20. The elastic information display device according to claim 19, wherein the two items of elastic information are elasticity modulus and viscoelasticity modulus.

21. The elastic image display device according to claim 13, wherein the elastic image constructing means constructs the one elastic image by converting the different plurality of items of elastic information into an evaluated value for evaluating malignancy, and allocating a hue or luminance of each pixel in accordance with the evaluated value of each item of elastic information.

22. The elastic image display device according to claim 13, wherein the elastic image constructing means constructs the one elastic image by comparing and presenting different plurality of items of elastic information in the same set target region with at least one of numerical values, line maps and diagrams.

23. The elastic image display device according to claim 22, wherein the one elastic image is displayed by converting different plurality of items of elastic information in the target region into an evaluated value of malignancy, and comparing the evaluated value of the plurality of items of elastic information using bar charts.

24. The elastic image display device according to claim 22, wherein the one elastic image is an image wherein time variation of the different plurality of items of elastic information in the target region are displayed using a line map so as to compare them.

* * * * *